(12) United States Patent
Ray et al.

(10) Patent No.: US 7,989,779 B1
(45) Date of Patent: Aug. 2, 2011

(54) UNIVERSAL DOOR HANDLE SANITIZER DEVICE

(76) Inventors: David A. Ray, Peoria, AZ (US); Martin M. Abitzsch, Peoria, AZ (US)

( * ) Notice: Subject to any disclaimer, the term of this patent is extended or adjusted under 35 U.S.C. 154(b) by 235 days.

(21) Appl. No.: 12/321,851

(22) Filed: Jan. 27, 2009

Related U.S. Application Data

(60) Provisional application No. 61/065,467, filed on Feb. 13, 2008.

(51) Int. Cl.
*A61L 9/20* (2006.01)
*A61L 2/00* (2006.01)
(52) U.S. Cl. ............ 250/455.11; 250/504 R; 250/493.1; 422/24; 422/186.3
(58) Field of Classification Search ............. 250/455.11, 250/504 R, 493.1; 422/24, 186.3
See application file for complete search history.

(56) References Cited

U.S. PATENT DOCUMENTS

| 3,314,746 | A | * | 4/1967 | Millar | 422/186 |
| 4,710,634 | A | * | 12/1987 | Brookes | 250/455.11 |
| 6,298,521 | B1 | | 10/2001 | Butterfield | |
| 7,175,807 | B1 | * | 2/2007 | Jones | 422/24 |
| 7,598,501 | B2 | * | 10/2009 | Jones | 250/455.11 |

* cited by examiner

*Primary Examiner* — Nikita Wells
(74) *Attorney, Agent, or Firm* — Harpman & Harpman

(57) ABSTRACT

A universal ultraviolet light sanitation device that can be mounted to existing doors and the like wherein the UV light sources are positioned for treatment of a door knob or handle. The device provides for opposing UV lights in a light emitting housing around the doorknob. Sensor means within the assembly determines the non-presence of the user's hand and activates the UV lights before and after handle contact assuring sanitation of the light exposed non-porous surfaces.

5 Claims, 3 Drawing Sheets

UNIVERSAL DOOR HANDLE SANITIZER DEVICE

This application claims the benefit of U.S. Provisional Application No. 61/065,467, filed Feb. 13, 2008.

BACKGROUND OF THE INVENTION

1. Technical Field

This invention relates to sanitizing devices for contact surfaces such as ultraviolet lights (UV) which when positioned on or placed over a non-porous surface effectively sterilizes and sanitizes the surface as well as other sanitizing devices such as spray disinfectant applications.

2. Description of Prior Art

Prior art devices of this type have used a variety of different ultraviolet mounted lights to reduce or eliminate surface dwelling micro-organisms commonly found in our environment. Such devices prevent the spread of such pathogens passed on by contact by the utilization of direct exposure to ultraviolet lights, see for example U.S. Pat. Nos. 4,710,634, 6,298,521, and 7,175,807.

U.S. Pat. No. 4,710,634 is directed to a door handle sanitizing device for restrooms using a UV light source above a push plate handle surface which when activated sanitizes the exposed surfaces.

U.S. Pat. No. 6,298,521 claims a doorknob sanitizing device having a disinfectant vapor dispenser surrounding the doorknob shaft.

U.S. Pat. No. 7,175,807 illustrates a sterilization device for gripping surfaces having an integrated access handle with UV lights as a replacement element for existing access doors.

SUMMARY OF THE INVENTION

A universal ultraviolet light sterilization device that can be selectively mounted to a variety of existing doors which provides multiple ultraviolet light sources within which are controlled by motion sensing technology in a pre-programmed manner to sterilize the exposed non-porous surface of the doorknobs around which it is placed.

DETAILED DESCRIPTION OF THE INVENTION

Figure 1:
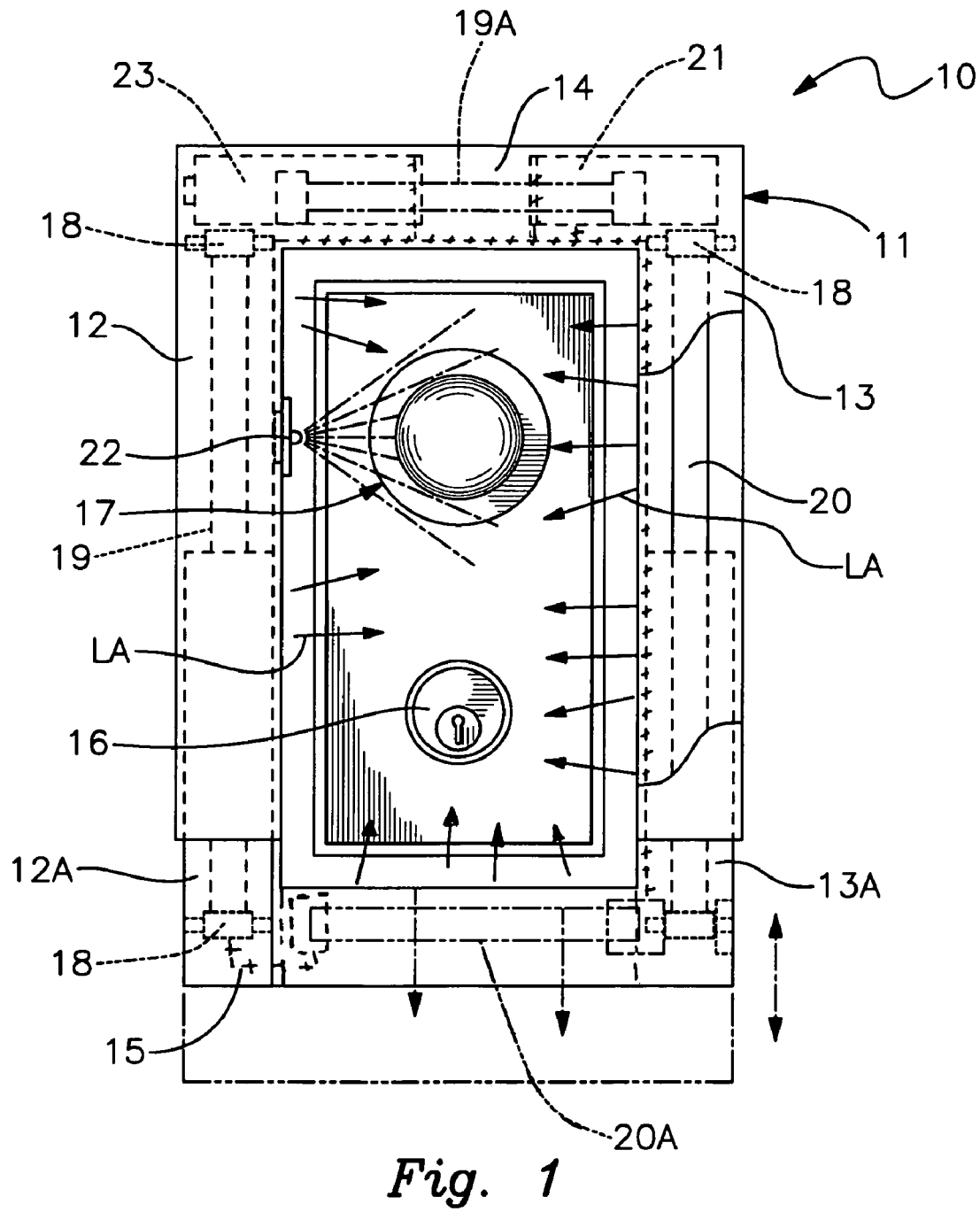
FIG. 1 is a front elevational view of the door handle sanitation device of the invention.
Figure 2:
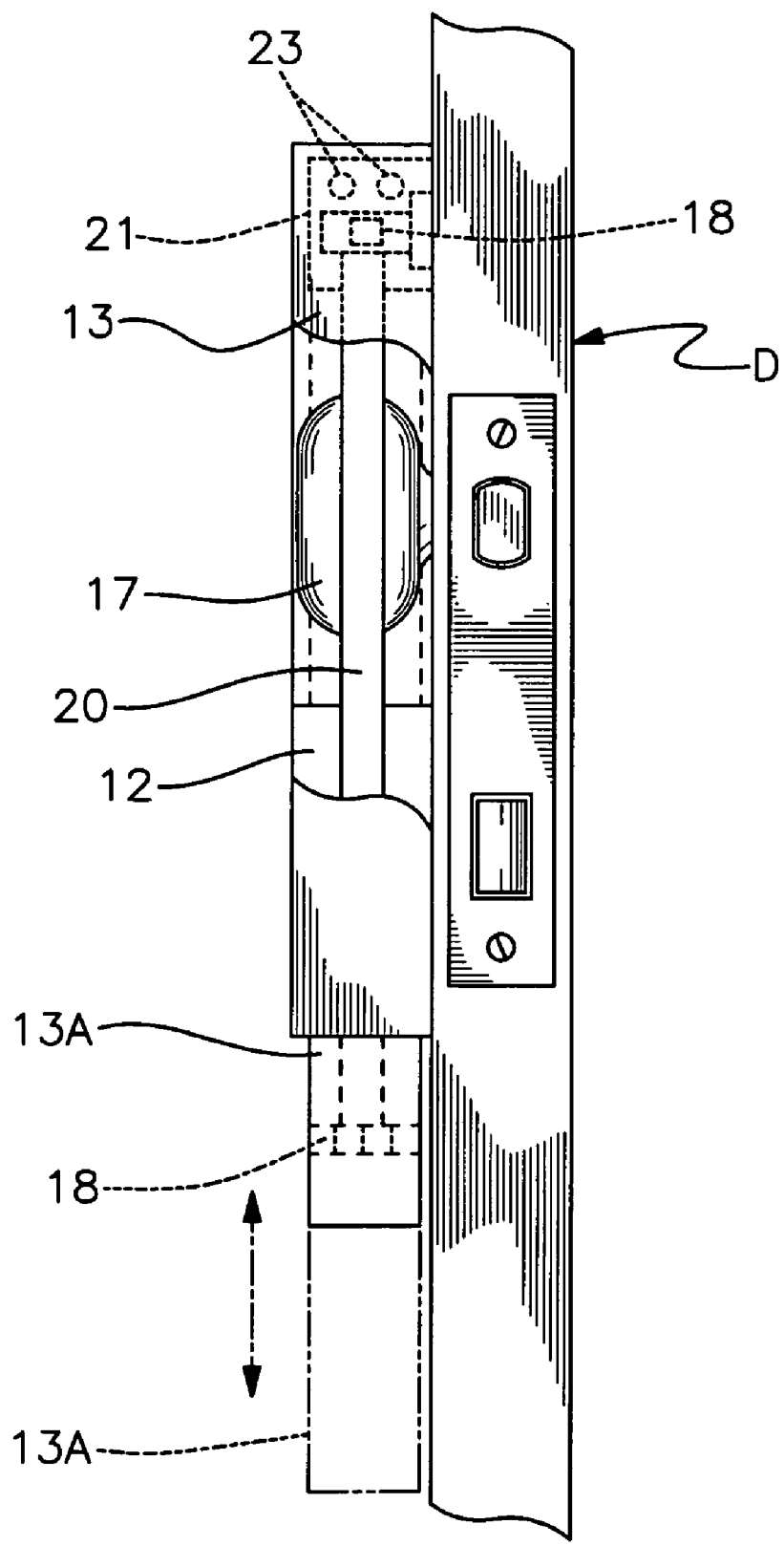
FIG. 2 is a side elevational view thereof.
Figure 3:
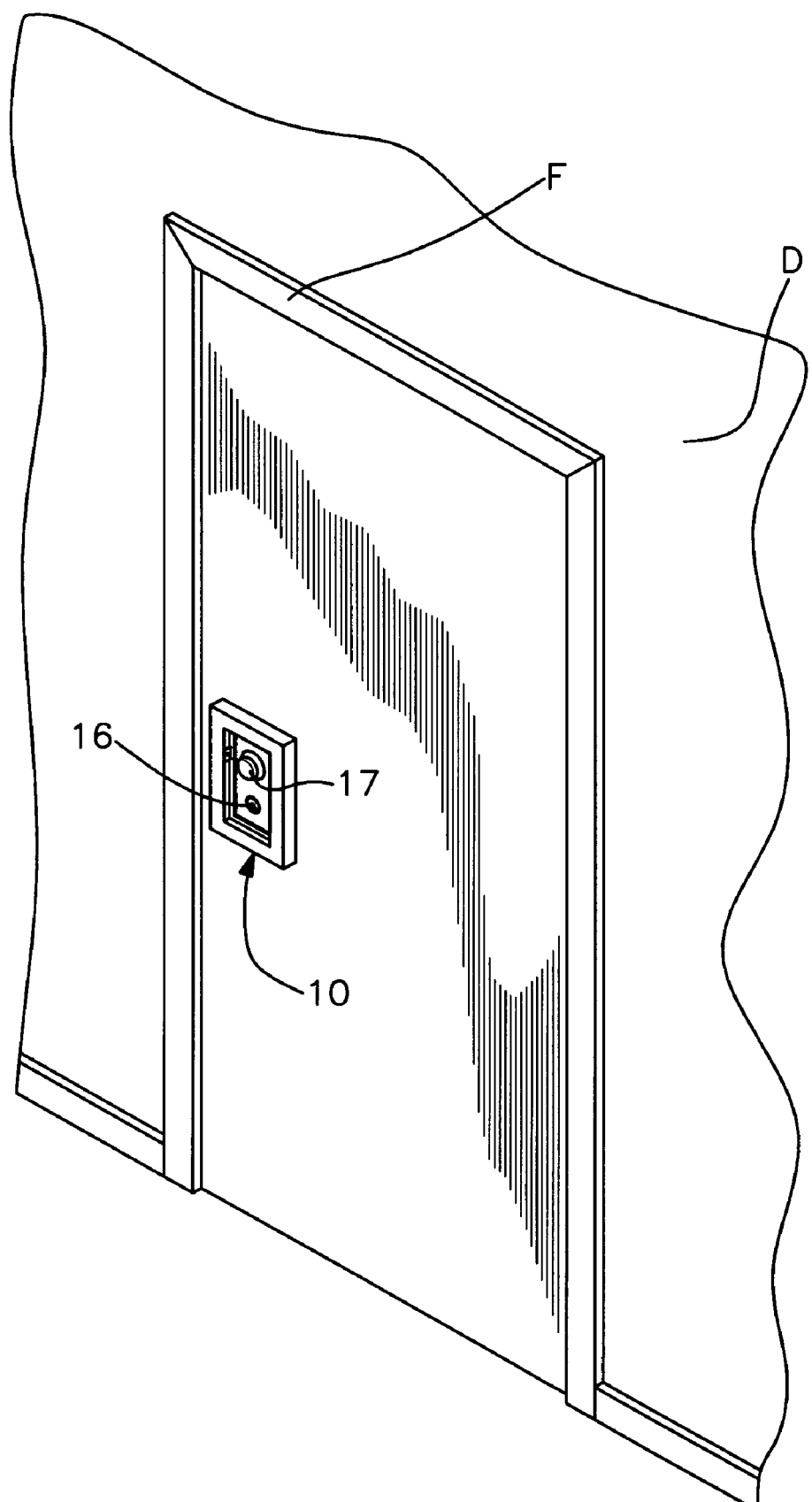
FIG. 3 is a graphic perspective view of a door with the device of the invention installed thereon.

Referring to FIG. 1 of the drawings, a universal doorknob/handle sanitation device 10 of the invention can be seen having a generally rectangular main housing 11 with oppositely disposed spaced parallel elongated side light enclosures 12 and 13. The enclosures 12 and 13 are interconnected by integrated top and bottom parallel enclosures 14 and 15 which defined in combination the housing 11. The bottom enclosure 15 is adjustable as indicated in broken lines by telescopically extensible sliding housing elements 12A and 13A allowing for adjustable increase in longitudinal length of the housing 11 to accommodate a wide variety of doorknobs/handles 17 and locks 16 combination.

Each of the side enclosures 12 and 13 have mounting sockets 18 for electrically connecting and holding a pair of elongated ultraviolet light bulbs 19 and 20 therein respectively.

Portions of the housing 11 facing the doorknob/handle 15 are transparent so as to allow UV light generated by the respective UV bulbs 19 and 20 to shine directly on the doorknob/handle 17 from opposite sides as indicated by light directional arrows LA.

It will be evident to those skilled in the art that non-porous surfaces exposed to ultraviolet light for a preset time are effectively sanitized by the killing of disease carrying pathogens given the exposure to UV rays generated by the UV light bulbs. To provide operational efficiency and automatic sanitation light activation control assembly 21 is provided having an electronic control circuit including and connected to a motion sensing switch 22 which mounted, in this example, in the side enclosure 12 so as to be de-activated upon the proximity of a user's hand (not shown) entering its sensing field indicated by broken lines in FIG. 1 of the drawings.

The electronic control circuit associated with the control device is programmed to activate and power the UV lights 19 and 20 after control input from the sensing switch 21 from an electrical power source which in this example is a battery 23 indicated in dotted lines in FIG. 1 of the drawings.

The sanitation device of the invention may also include additional ultraviolet light bulbs indicated at 19A and 20A in broken lines which in this example would be positioned in the corresponding top and bottom interconnecting enclosures 14 and 15 above and below the doorknob handle 17. As noted, in use, once activated, the UV lights 19, 19A, 20 and 20A will shine directly on the doorknob/handle 15 sanitizing its light exposed surface. Upon notice, the motion sensing switch 21 and the integrated control circuit for the UV lights will be de-activated by detected presence. The sanitation device 10 of the invention can be used on any existing doorknob/handle 17 due to its universal mounting design surface and adjustable features hereinbefore described.

Additionally, a non-battery powered source could be adapted to supply operational power or recharge the batteries 23 when the door D is in closed position by an integrated low voltage contact conductors C mounted on the door D and the associated contact door frame F from a continuous source of adapted AC power in a new construction situation or in a remodel retro-fit if so desired as will be understood by those skilled in the art.

It will thus be seen that a new and novel doorknob/handle sanitation device 10 of the invention has been illustrated and described and it will be apparent to those skilled in the art that various changes and modifications may be made thereto without departing from the spirit of the invention.

We claim:

1. A door handle sanitation device comprising an adjustable housing secured about a door handle,
   multiple sources of UV radiation within said housing,
   said multiple sources of UV radiation are ultraviolet light bulbs,
   a sensor switch in communication with a control circuit and said sources of UV radiation,
   said ultraviolet light bulbs in parallel spaced opposing pairs about said door handle,
   means for selectively adjusting said housing about said door handle and a power source for said control circuit and said sources of UV radiation.

2. The door handle sanitation device set forth in claim 1 wherein portions of said housing are transparent adjacent said sources of UV radiation.

3. The door handle sanitation device set forth in claim 1 wherein said sensor switch comprises,
 a motion control switch positioned adjacent said door handle responsive to close proximity motion.

4. The door handle sanitation device set forth in claim 1 wherein said control circuit activates said sources of UV radiation in response to said sensor switch for a predetermined time sufficient to sterilize all exposed surfaces of said door handle simultaneously.

5. The door handle sanitation device set forth in claim 1 wherein said means for selective adjusting of said housing comprises,
 a bottom enclosure portion movable from a first position to a second position in spaced relation to said door handle, by telescopic extension of parallel side light enclosures in communication therewith.

\* \* \* \* \*